(12) United States Patent
Lyon

(10) Patent No.: US 6,770,483 B2
(45) Date of Patent: Aug. 3, 2004

(54) DETERMINATION OF MULTI-VALENT METAL CONTAMINATION AND SYSTEM FOR REMOVAL OF MULTI-VALENT METAL CONTAMINANTS FROM WATER

(76) Inventor: Irving Lyon, 3529 Greenfield, Los Angeles, CA (US) 90034

(*) Notice: Subject to any disclaimer, the term of this patent is extended or adjusted under 35 U.S.C. 154(b) by 0 days.

(21) Appl. No.: 09/739,536

(22) Filed: Dec. 15, 2000

(65) Prior Publication Data

US 2002/0108910 A1 Aug. 15, 2002

(51) Int. Cl.$^7$ ............................................. G01N 33/18
(52) U.S. Cl. ............................. 436/39; 436/73; 436/41; 436/84; 436/83; 210/719; 210/94
(58) Field of Search .......................... 436/73, 39, 41, 436/84; 210/719, 94

(56) References Cited

U.S. PATENT DOCUMENTS 5,000,859 A * 3/1991 Suciu et al. ................ 210/713

* cited by examiner

*Primary Examiner*—Jill Warden
*Assistant Examiner*—Sam P. Siefke (57) ABSTRACT

A test for determining the presence of multi-valent metal contaminants, such as arsenic, mercury and chromium, when present in certain valence states and a system for removal of these contaminants from water. Multi-valent metal salts, for example, $Cr^{+6}$, which are highly toxic, can be detected and potentially removed from water through a redox reaction by reaction with iron or cobalt salts to obtain a reductive elimination of the $Cr^{+6}$ by conversion to $Cr^{+3}$. The determination may be in the form of a test, such that a tableted composition can be introduced into water for reduction of a metal salt, such as $Cr^{+6}$ to $Cr^{+3}$ in order to provide a visual indication thereof. The system for the conversion of $Cr^{+6}$ or other reducible metal salts to other lower valence states having less toxicity would rely upon introduction of a metal salt in the form of a reducing agent which would be introduced into the water allowing for a reduction/oxidation action to take place. This would be followed by removal of the flocculated/precipitated reduced contaminant metal salt and by re-reduction of the oxidized reducing agent.

43 Claims, 1 Drawing Sheet

DETERMINATION OF MULTI-VALENT METAL CONTAMINATION AND SYSTEM FOR REMOVAL OF MULTI-VALENT METAL CONTAMINANTS FROM WATER

BACKGROUND OF THE INVENTION

1. Field of the Invention

This invention relates in general to new and useful improvements in a determination for the presence of water-soluble toxic reducible metals and metal salts in water and a method for removal therefrom and, more particularly, to a method for determining the presence of toxic metal salts and a system for the removal of such metal salts from drinking water which relies upon a reduction of the metal salt in a reduction/oxidation reaction to a different valence state and which would enable determination of the presence and allow for removal of the contaminant.

2. Brief Description of the Related Art

It is well established that water and, particularly, municipal drinking water, as well as water from aquifers and wells, presently contain trace amounts of highly toxic metals, including, for example, arsenic, mercury and chromium. Each of these metals are usually present in the form of various metal salts in different oxidized states and are known to be either carcinogens or otherwise known to present significant health risks.

Chromium is an example of a metal present as a metal salt contaminant found in many water sources. Two of the most common forms of chromium are trivalent chromium ($Cr^{+3}$), and hexavalent chromium ($Cr^{+6}$), although chromium can exist in other valence states, such as $Cr^{+5}$, $Cr^{+4}$ and $Cr^{+2}$. It is also known that salts containing metals, such as $Cr^{+3}$ are relatively harmless while salts of $Cr^{+6}$ are highly toxic. Many of these metals and metal salts, such as $Cr^{+6}$ and $Cr^{+6}$ compounds are not normally present as natural constituents of environmental media, and their presence is almost always the result of human activity, including commercial and industrial processes, which generate $Cr^{+6}$ and its salts and release them into the environment. As an example, cooling towers and ancillary equipment, catalysts used in the cracking and refining of petroleum products, tanning, textile dying, etc., are some of the commercial and industrial processes which give rise to these oxidized metals and their salts, such as those of $Cr^{+6}$.

It is also known that many of these metals and their salts, such as $Cr^{+6}$, which may be airborne, can induce lung cancer through inhalation. The presence of $Cr^{+6}$ is not only recognized as a toxic substance, but its presence in drinking water is limited by current U.S. government standards with a maximum contaminant level of 0.1 milligrams per liter (100 parts per billion). In the State of California, USA, the standard for chromium in drinking water is 50 parts per billion. A present proposal suggests that even these standards are too lax and that the maximum allowable amount of total chromium present should be no more than 2.5 parts per billion. There have even been studies which suggest that the maximum amount of $Cr^{+6}$ which should be allowable in drinking water should be no more than 0.2 parts per billion.

The seriousness of the health consequences of these oxidized metals and metal salts, when present in drinking water have been studied. It has been found that $Cr^{+6}$, for example, can be distributed throughout the body and accumulates in the kidney, spleen and pancreas. Uptake of $Cr^{+6}$ into the liver is 40 to 90 times that found in other organs. While $Cr^{+3}$ does not readily enter the cells of these organs, $Cr^{+6}$ does so. Within cells, $Cr^{+6}$ is reduced stepwise to $Cr^{+5}$, $Cr^{+4}$, and $Cr^{+3}$. During this process, aberrant forms of oxygen, including hydroxyl free radicals, OH, and the superoxide anion, $O_2^-$, are produced as potent toxins. These potent toxins can cause chemical changes in cellular DNA, i.e., mutations, leading to severe alterations in cell functions and carcinogenic effects. Other effects of these $Cr^{+6}$-induced toxins result in a potent genotoxic agent. Still other effects of these $Cr^{+6}$-induced toxins result in compromising the body's immunoprotective systems and they can act as neurotoxins. In addition, they can cause developmental and reproductive damage, not to mention other adverse conditions and maladies caused by their presence.

Although it would be desirable to advise the public of the presence of metals and their metal salts in water, and particularly those which are toxic, no convenient test is currently available to detect their presence. Many of these oxidized metals are not visible at low concentrations, cannot be tested directly and easily and are otherwise sensibly indeterminable. Nevertheless, determination of the presence of metal toxic substances in water by the public in general would be desirable.

The prior art has usually involved the removal of $Cr^{+6}$ and other toxic oxidizable metals by providing a reducing agent or reductant as a source of electrons. These agents reduce these metals to a lower valence state, one which is often non-toxic or less toxic. However, precipitation of $Cr^{+6}$, for example, by control of pH alone is insufficient to remove chelated or complexed forms of $Cr^{+6}$ or other heavy metals. There have been attempts to use controlled pH methods supplemented with flocculents or precipitants to allow for the removal of $Cr^{+6}$ through flocculation, precipitation and settling out followed by filtration.

Reduction of $Cr^{+6}$ to $Cr^{+3}$ does eliminate the toxic hexavalent form of the metal by converting it to the essentially non-toxic form of $Cr^{+3}$ by the reaction:

$$Cr\ VI + 3\ e's \underset{\text{oxidation}}{\overset{\text{reduction}}{\rightleftarrows}} Cr\ III \qquad 1)$$

Conversion of the Cr from a higher valence state to a lower valence state is accompanied by oxidation of the reducing agent or reductant from a corresponding lower valence state to a higher valence state. The combination of these two reactions constitutes a coupled redox reaction.

There have been several attempts and proposals for removal of some of these oxidized metal contaminants from water including, for example, U.S. Pat. No. 4,149,953 to Rojo, which relies upon an electrolytic cell to remove impurities. An anode of this cell containing aluminum particles and a cathode containing iron particles operates with the water serving as an electrolyte. The aluminum and iron particles which enter the water function as flocculents and adsorb impurities in the water. The flocculated materials are then separated from the water by conventional means. Application of this type of system to waste, process or drinking water for removal of $Cr^{+6}$ or other oxidized metals is limited because it may bring down the chromium in the flocculate without necessarily reducing the metal. Moreover, this type of process would be difficult to implement, would not be efficient and would be costly to operate. Thus, the desirable conversion of $Cr^{+6}$ to $Cr^{+3}$ and subsequent removal of the latter as a precipitate, may not result.

U.S. Pat. No. 4,693,798 to Gale and O'Donnell discloses use of an electrolytic cell for generation of $Fe^{+2}$ ions in an acidified medium. The $Fe^{+2}$ interacts with $Cr^{+6}$ ions reducing them to $Cr^{+3}$ ions. However, a part of this stream is bled off into the contaminated stream containing $Cr^{+6}$ ions. This must be followed by alkalinization of the treated stream of water to a pH in excess of 7.5 to allow for coprecipitation of $Cr^{+3}$ and $Fe^{+3}$ hydroxides.

Another system for waste water treatment is described in U.S. Pat. No. 4,923,599 to Bowers. In the system described in the Bowers patent, a controlled volume of waste water containing heavy metals and including, for example, $Cr^{+6}$, is treated by optimizing and controlling pH to cause precipitation of some of the heavy metal contaminants. This is followed by filtration and monitoring of the samples' turbidity to determine the amount of additional precipitating agent which may still be needed. Although a claimed advantage of this method is the reduction in the amount of resultant sludge, this system must be operated continuously so as to be most effective in achieving a predetermined set point of heavy metal concentration in solution. Moreover, it is not very effective and still leaves substantial amounts of trace heavy metals in the water.

U.S. Pat. No. 5,000,858 to Manning and Wells sets forth a method for removing hexavalent chromium from water which employs two or more reactors for treating waste water. Each reactor contains a flocculator and a clarifier for batch treatment in an acidic medium below a PH of 3. A reducing agent is added and the pH is thereafter increased to an alkaline pH where the water is then transferred to the second reactor having a flocculator. In this case, a flocculent is added and the solution is then transported to a clarifier where the heavy metal-containing solids are removed.

U.S. Pat. No. 5,000,859 to Suciu, et al discloses a process in which a sodium sulfide/ferrous sulfate treatment is used to remove hexavalent chromium, as well as other potentially toxic metals, from industrial waste waters. This patent discloses the use of sulfur dioxide, sodium sulfite, sodium bisulfite, sodium borobydride, and the use of ferrous ions as reducing agents. This method relies upon reduction of $Cr^{+6}$ to $Cr^{+3}$ in a pH range of about 7 to 9 by addition of ferrous ions from ferrous sulfate followed by sulfide or more ferrous ions to induce precipitation of the $Cr^{+3}$ and of other reduced heavy metals. Polymers are added to aid flocculation of the reduced metals by formation of a precipitate or sludge and to clarify the waste stream.

U.S. Pat. No. 5,045,213 to Bowers also sets forth a waste water treatment for removal of metals by precipitation and filtration. The pH levels are optimized to precipitate the metals from the water samples and continuous sampling is used to determine presence of unprecipitated metals still remaining in solution. The metals in the water are treated with a Group II metal dithiocarbamate precipitating agent to precipitate chelated and/or complexed metal in the waste water stream unaffected by pH control. In addition, and in accordance with Bowers, it may be necessary to use a pre-treatment in order to reduce the amounts of the dithiocarbamate precipitants.

U.S. Pat. No. 5,370,827 to Grant, et al sets forth a method of solution decontamination in which heavy metal-containing water is treated with precipitants, such as sodium silicate and ammonium hydroxide. The pH of the contaminated solution is adjusted to about pH 5 to about pH 9.5 using hydrochloric acid. The resultant gels polymerize and/or precipitate the contaminant-containing silica matrix which forms a separable solid easily removed from the water by filtration.

U.S. Pat. No. 5,380,441 to Thornton describes a procedure for removal of chromium with mechanically agitated iron particles. The $Cr^{+6}$ is converted to $Cr^{+3}$ and precipitated with $Fe^{+3}$ hydroxides. Solution pH is maintained in an acid range of 2 to 7 during the reduction of the chromium, and the pH thereafter is readjusted with base to facilitate the formation and precipitation of chromium hydroxide.

Although the removal of these toxic oxidized metals and metal salts is a problem which must be addressed by governmental agencies and industry, the consumer should at least be aware of the potential presence of these metals and metal salts in their drinking water. Thus, it would be desirable to provide a simple test to determine the presence of such highly toxic metals and metal salts. Even more so, it would be desirable to provide a process which is effective for the removal of $Cr^{+6}$ and other oxidized metals from drinking water which can be performed at relatively low cost and high efficiency.

OBJECTS OF THE INVENTION

It is, therefore, one of the primary objects of the present invention to provide a visual determination which allows unskilled personnel to automatically and easily detect the presence of metal contaminants in water.

It is another object of the present invention to provide a method of allowing testing of drinking water for the presence of metals and metal salt contaminants visually by addition of a simple tablet thereto.

It is a further object of the present invention to provide a method for reduction of metals and metal salts to a reduced valence state allowing for precipitation of potentially toxic metals from a stream of water.

It is an additional object of the present invention to provide a method of providing a stream of drinking water through removal of $Cr^{+6}$ and other oxidized metal contaminants by using a reduction reaction for reducing a metal contaminant in the presence of a reducing agent.

It is still another object of the present invention to provide a method of removal of oxidized metal constituents in water by the addition of a reducing agent in which a reduction/oxidation reaction takes place along with removal of the precipitated and reduced metal constituents, as well as co-reduction of the oxidized reducing agent.

It is still a further object of the present invention to provide both a process for testing and a process for removing metal contaminants from water in a relatively inexpensive but highly efficient manner.

With the above and other objects in view, my invention resides in the novel features of form, construction, arrangement and combination of parts and components presently described and pointed out in the claims.

SUMMARY OF THE INVENTION

1. Basic Principles of the Invention

The present invention first relates to a composition for the detection of oxidized metal contaminants in drinking water. In this respect, the term "oxidized metal" will refer to metals and metal salts. In addition, the term "oxidized" will refer to those metals which are multi-valent and can exist in an oxidized state, that is have a higher valence state than other valence states for that metal. For example, $Cr^{+6}$, the highest oxidized state of this metal, can exist in reduced valence states, such as $Cr^{+5}$, $Cr^{+4}$ or $Cr^{+3}$.

The testing of water is preferably conducted with a three-component system, such that the three components may be added individually or together, in the form of a tablet, to a sample of water. In accordance with this aspect of the invention involving the detection of metals, such as hexavalent chromium, the first component is a reducing agent in the form of a water-soluble metal salt having the capability of existing in an oxidized metal state and in a reduced metal state. For example, iron in its ferrous form, $Fe^{+2}$, provides electrons for the reduction of $Cr^{+6}$ to $Cr^{+3}$. Similarly, other metal constituents would be converted to their reduced metal salt forms. In these processes, ferrous iron, $Fe^{+2}$, is oxidized and converted to ferric iron, $Fe^{+3}$. Generally, for the conversion of $Cr^{+6}$ to $Cr^{+3}$, a water-soluble ferrous salt, like ferrous sulfate, may be used.

The second component in this three-component system is an acidifying substance, for example, citric acid or another tri-carboxylic acid. The acidifying component assures solubility of oxidized chromium salts present in drinking water and forms a stable complex with ferrous iron.

The third component is a mixing aid, such as sodium bicarbonate, which, in the presence of the acidifying component, facilitates the break-up of the tablet, and allows its components to rapidly diffuse throughout the sample of water being tested, thereby speeding up the redox reaction.

In accordance with this method, the oxidized metal, such as the $Cr^{+6}$, for example, is reduced to $Cr^{+3}$, while the $Fe^{+2}$ in ferrous sulfate is converted to $Fe^{+3}$. The products of these redox changes lead to co-precipitation of $Cr^{+3}$ and $Fe^{+3}$ in the form of insoluble mixed hydroxides. The change in valence states of the chromium and iron result in water turbidity and color changes which allow for the easy visual determination of the presence of the toxic metal constituent.

The present invention also provides a method of removal of heavy metal contaminants from water through essentially the same chemical process. In this case, the metal in the water is treated with a reducing agent involving minimal intervention. This is followed by removal of the precipitated metal when reduced and the re-reduction of the oxidized reducing agent.

More specifically, in connection with the method of treating water, a reducing agent is added in an acidified medium. Thereafter, and following a redox reaction involving reduction of the metal contaminant and coupled oxidation of the reducing agent, the pH would again be raised to an alkaline level through the addition of a base. Clarifying agents, such as flocculents and/or precipitants are then added to provide for the removal of the aggregated reduced and generally precipitated toxic metal constituent. In addition, electrons could be introduced through an electrical conductor into the treated water to reduce the oxidized reducing agent and to maintain the precipitated contaminant in a reduced valence state. This inflow of current (electrons) would be accompanied by an inflow of hydrogen ions (protons) along a separate conduction path to re-establish and maintain the pH in a desired acid range, for example, between 2.4 to 6.5.

In particular, the invention is primarily directed to, although by no means limited to, reduction of $Cr^{+6}$ to $Cr^{+3}$ in a stream of water by use of a reducing agent, such as $Fe^{+2}$, e.g. ferrous sulfate. In the reduction reaction, the ferrous sulfate is converted to an oxidized form of iron by a transference of electrons, and the chromium is correspondingly reduced. The lower valence state of the metal contaminant obviously corresponds to the reduced state of the metal, and the higher valence state of the reducing agent is produced as a consequence of yielding electrons contributed by the metal atom of the reducing agent which then becomes oxidized.

Solubility of the metal contaminant while in its oxidized form, e.g. $Cr^{+6}$, may be either higher or lower than the reduced form of that same metal salt. Obviously, if the solubility of $Cr^{+6}$ is higher, the lower solubility of the reduced form of the salt ($Cr^{3+}$) will facilitate co-precipitation with the oxidized metal constituent of the reduction agent. $Cr^{+6}$ is known to have a higher solubility in aqueous media than $Cr^{+3}$. The same holds true of the reducing agent, in that it may have lower solubility in its oxidized form. In the case of the reduced $Cr^{+6}$, this co-precipitate may exist in the form of $Cr^{3+}$ and $Fe^{3+}$ mixed hydroxides at pH's above 7.0. If the solubility of the reducing agent is higher, some of the oxidized form of the reducing agent salt will remain in solution where, after removal of the precipitated material, it can be easily re-reduced by electrons introduced into the reaction media.

The preferred reducing agents are generally selected salts of these metals and they must have the necessary solubility properties. The metal salt reducing agents must also involve metals capable of existing in two or more valence states, such as an oxidized metal atom state and a reduced metal atom state. The anions of the metal salt reducing agents may include acetates, chlorides and other halides, nitrates, sulfates, etc. Moreover, the hydrates of these salts are usually more soluble in water then their non-hydrated congeners.

2. Character and Advantages of the Invention

The invention can adopt the form of a cyclic process during which di-, tri-, and/or polyvalent metal salts acting as reducing agents convert toxic polyvalent metal contaminants, e.g. chromium (Cr VI), in water, including drinking water, to non-toxic lower valence state metal salts, e.g. chromium (Cr III). In this process, the metal salts of the reductants are oxidized while the chromium salts are reduced. The process is driven by a fuel cell that continuously regenerates these reducing agents, thereby making this a recyclable activity. This same process can be used to remove arsenic and mercury and their salts from various sources of water. Although the invention is operable with other metal components, it will be described in terms of conversion of Chromium VI to Chromium III.

Removal of the trivalent chromium (Cr III), and of the relatively small quantities of the oxidized reducing agents, as mixed insoluble hydroxides, necessitates the periodic replenishment of the small fraction of these reducing agents lost during this recycling process.

The advantages of this process derive from its simplicity, visual control, and recyclable nature. This insures that human intervention will be minimal. Personnel will not require extensive training to become effective operators of this system. Nor will their training require extended periods of time or expensive training materials to qualify and to be certified as operators. Replacement costs, including those of the metal salt reductants, and acids and bases used for automated and pre-programmed pH adjustments, as well as costs involved in operation and maintenance, will also be minimal.

The efficiency of the reducing process may be enhanced by mixtures of reductants, especially of salts of metals belonging to the same or closely related chemical groups in the Periodic Table.

The recyclable character of the overall process is dependent on three subordinate cycles: (1) the redox cycle of the metal salt reductants; (2) the automated and preprogrammed acidification—alkalinization cycle to maintain selected pH ranges; and (3) operation of a fuel cell.

The preferred fuel for the fuel cell is hydrogen produced by the electrolysis of water. However, methane and/or other low molecular weight alkanes may be used to produce the hydrogen. The burning of these fuels in the fuel cell would produce a stream of protons for the control of pH. The accompanying but separate stream of electrons would facilitate the re-reduction of the oxidized reductants following conversion of Cr VI to Cr III, respectively, with minimal adverse environmental impacts. The streams of protons and electrons would be conducted directly from the fuel cell along two different conduction paths into the main chamber of the reactor.

This invention possesses many other advantages and has other purposes which may be made more clearly apparent from a consideration of the forms in which it may be embodied. These forms are shown in the FIGS. 1 and 2 forming a part of and accompanying the present specification. They will now be described in detail for purposes of illustrating the general principles of the invention. However, it is to be understood that the following detailed description is not to be taken in a limiting sense.

BRIEF DESCRIPTION OF THE FIGURES

Having thus described the invention in general terms, reference will now be made to the accompanying figures wherein:

DETAILED DESCRIPTION OF PREFERRED EMBODIMENT

1. Testing Compositions

Referring now in more detail to the invention, there is first provided a test for determining the presence of an oxidized metal contaminant in drinking water used in industrial or commercial processes, or founed in waste water. It is known that when a reducing agent, such as a ferrous salt or a colbaltous salt, is added to drinking water in which hexavalent chromium ($Cr^{+6}$) may be present, colors of various tints or shades will form. Thus, color tints which are lighter, and/or shades which are darker, tinged with a yellow, red, brown or blue-green cast will appear when viewed against a white background. The intensity of the color depends both upon the nature and concentration of the reducing salt used and upon the nature and concentration of the toxic metal contaminant, such as $Cr^{+6}$.

The color which develops in accordance with the reduction of the metal contaminant and oxidation of the metal reductant appears to form fairly quickly and is associated with a suspension of fine particles developed in the water after the addition of the reducing salt, such as the ferrous salt or the cobaltous salt. Thereafter, the color is stable. When mixed with the reducing salt, the metal constituent, i.e., the contaminant, is easily detected by visual examination at very low concentrations, e.g. 0.1 part per billion. The color change does not necessarily occur with the reduced form of the metal contaminant, for example, with trivalent chromium ($Cr^{+3}$).

The test for the determination of the presence of a metal contaminant in the water will be described in connection with the presence of $Cr^{+6}$, which is one of the most highly toxic, but yet readily detectable, contaminants in water. However, it should be understood that the invention is equally applicable to determination of the presence of other metal contaminants, such as, for example, mercury and mercury salt contaminants and arsenic and arsenic salt contaminants. In substance, the invention is applicable to the testing and also treatment of any liquid which contains a water-soluble metal contaminant, in the form of a metal salt, capable of existing in both an oxidized (higher valence) state, as well as a reduced (lower valence) state.

One set of chemical reactions which describes this determination involving the reduction of hexavalent chromium ($Cr^{+6}$) to the essentially non-toxic trivalent chromium ($Cr^{+3}$) involves the use of an iron ($Fe^{+2}$) or cobalt metal reducing agent, such as $Co^{+2}$, which is then oxidized to ferric iron ($Fe^{+3}$) or the higher valence state of cobalt ($Co^{+3}$). In the process, the $Cr^{+6}$ is reduced to $Cr^{+3}$.

The reaction can be schematically described as follows:

| 2) | $3\ Fe^{2+} + Cr^{6+}$ | → | $3\ Fe^{3+} + Cr^{3+}$ |
|---|---|---|---|
|   | (ferrous) (hexavalent) |   | (ferric) (trivalent) |
| 3) | or $3\ Co^{2+} + Cr^{6+}$ | → | $3\ Co^{3+} + Cr^{3+}$ |
|   | (cobaltous) |   | (cobaltic) |

In the above reactions (2) and (3), the ferrous ions represent the reduced (Fe II) form of iron, as ferrous sulfate heptahydrate, $Fe(SO_4) \cdot 7H_2O$ having a formula weight of 278.01 daltons, or otherwise, a cobaltous compound (Co II) acetate tetrahydrate, $Co(C_2H_3O_2)_2 \cdot H_2O$, with a formula weight of 249.08 daltons. The source of the oxidized chromium, the contaminant, is frequently sodium chromate tetrahydrate as in the example above, $Na_2CrO_4 \cdot 4H_2O$ with a formula weight of 234.06 daltons. The reduced chromium ($Cr^{+3}$) often exists as chromium trichloride ($CrCl_3$) with a formula weight of 158.38 daltons.

When the reductant is added to water, it can be added in a relatively small amount as, for example, one ounce of ferrous sulfate to about one hundred milliliters of water. This yields a solution concentration of 1.02 molar Fe II. There is no specific required amount for the addition of the reducing agent, except that the reducing agent should be present in an amount of sufficient concentration to reduce essentially all of the reducible metal contaminant in the water. A simple series of dilutions can be used with an aliquot of the water to be tested to determine the desired range of concentration of the reductant. Alternatively, an aliquot of treated water can be pre-tested with additional reductant to see if any further change in color occurs.

A variety of reducing agents can be used in this determination and, incidentally, the same reducing agents would be used in the process, as hereinafter described. These reducing agents are usually maintained at an acidic pH between 2.5 to about 6.5 in order to maintain solubility of both the $Cr^{+6}$ and the converted $Cr^{+3}$. Some of the numerous agents which can be used include, for example, the iron-cobalt compounds; sulfites ($SO_3^{-2}$) and hydrogen sulfites ($HSO_3^-$); dithionites ($S_2O_4^{-2}$); reducing sugars, such as monosaccharides ($C_6H_{12}O_6$): galactose, glucose and mannose, and the various disaccharides ($C_{12}H_{22}O_{11}$): maltose and sucrose, etc. In addition, metallic iron ($Fe^0$) has also been used successfully as a $Cr^{+6}$ reducing agent. As indicated previously, the reduction of the chromium or other metal contaminants is also facilitated by a shift in pH toward an alkaline range, for example, to a pH of 7 and above. This is followed by flocculation and/or precipitation, and the removal of precipitates by settling out, followed by filtration or by other conventional means.

The determination of the presence of oxidized metal salt contaminants is preferably conducted by the addition of a three-component tablet which can be directly introduced into the drinking water. Alternatively, the individual powder or granular forms of the three components of the tableted composition can be added. The exact form of the components used for testing, whether tableted or not, is not critical in accordance with the present invention.

As indicated above, the composition for determination will include the reducing agent, such as the selected ferrous, cobaltous, or other lower valence metal salt. Secondly, the invention will include a sequestering agent, i.e., an agent which will stabilize the reducing agent. Preferably, this will involve the use of a dicarboxylic acid or tricarboxylic acid, including those mentioned above and hereinafter described. Further, the third component of the composition will be a salt which will break up the tablet quickly and enable rapid distribution of active ingredients throughout the water being tested. A salt which is effective for this purpose is one that will release a gas, such as carbon dioxide, in an acidic medium. Release of this carbon dioxide breaks up the tablet quickly and distributes the active ingredients throughout the water.

One particularly effective component that will break up the tablet quickly is sodium bicarbonate. The following equation indicates the reaction which takes place:

4)  R-COOH + NaHCO$_3$  →  RCOONa + H$_2$CO$_3$
    (carboxylic acid) (bicarbonate)    (carboxylate) (carbonic acid)

Inasmuch as the carbonic acid is not stable under ambient conditions, it will break down into water and carbon dioxide. The released carbon dioxide accelerates the break-up of the tablet.

2. Water Treatment

The process for conversion and removal of harmful or toxic metal constituents in water relies upon the same set of chemical reactions used in connection with the testing of drinking water. Generally, an in-line system capable of cyclic regeneration of the reducing agent would be employed. In this way, no new amount of or, at least, no substantial amounts of reductant would have to be added over a number of redox cycles, except for the reductant needed to replenish losses by co-precipitation with the $Cr^{+3}$ hydroxide which is formed.

The present invention could readily use a sealed reaction chamber using a batch-type treatment operation, or otherwise, it could be operated in a continuous flow system. One reactor which could be used in accordance with the present invention is illustrated in the accompanying FIG. 1, which shows a reactor 10 having an input port 12 for receiving the introduced stream of water to be treated. An outlet port 14 would be located at the lower end of the reactor for withdrawal of waste products, as hereinafter described. This port 14 could possibly be connected to one or more channels formed in the bottom of the reactor for carrying any waste constituents to this outlet port 14.

Figures 1, 2:
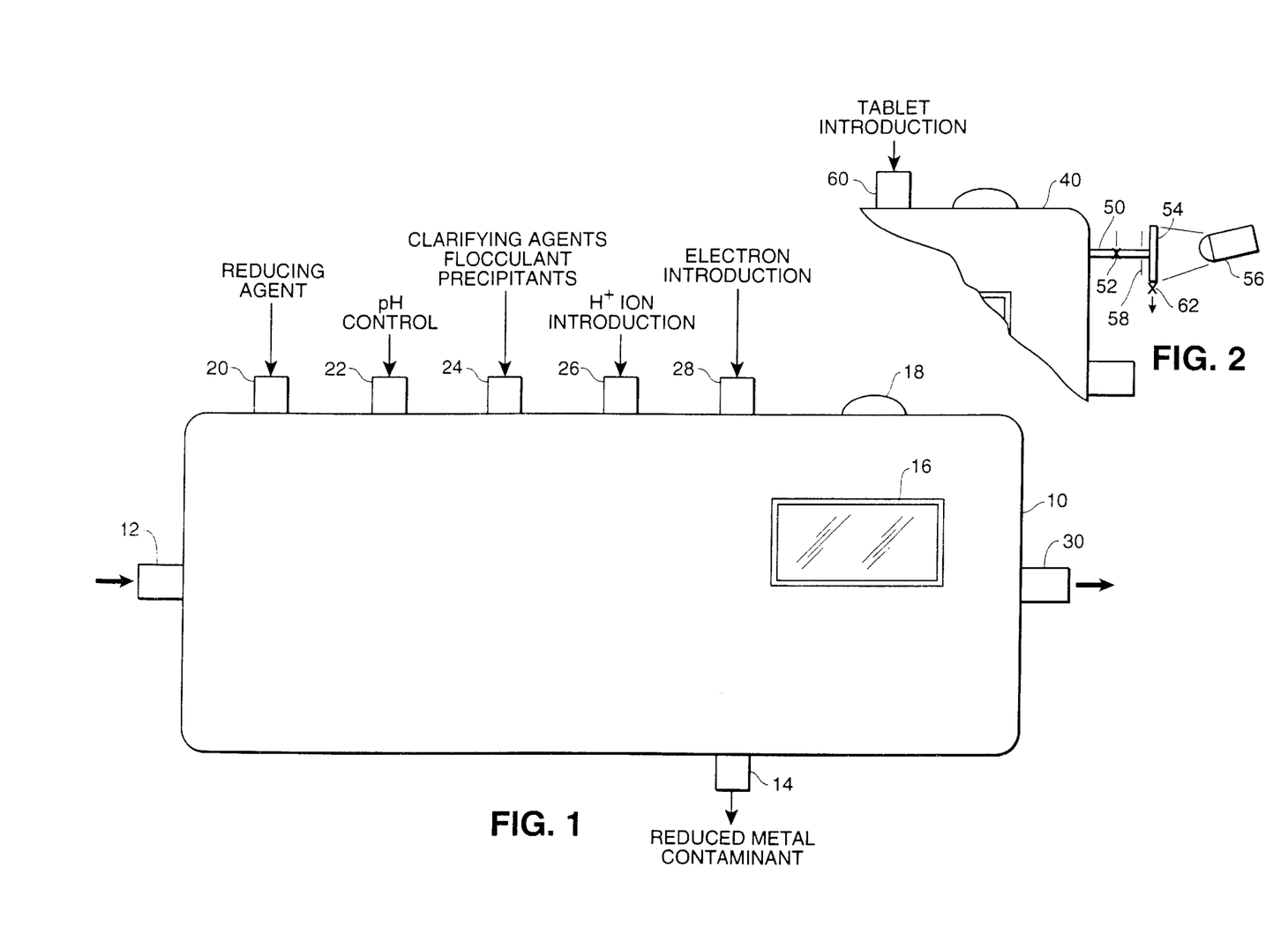
FIG. 1 is a schematic illustration of a reactor for reducing metal contaminants in water to non-toxic, reduced metal states.
FIG. 2 is a fragmentary schematic illustration of a modified form of reactor in accordance with the present invention.

The contents introduced into the reactor would be kept in constant motion to aid in distribution of reactive substances through the provision of a sealed magnetic stirring device (not shown). In addition, the reactor is preferably provided with a window 16 and a sealed source of light 18 for viewing changes in color taking place in the reaction medium. Alternatively, as hereafter described in more detail, in addition to the window, a small sample of the water being treated would be continuously diverted from the reactor's main chamber into a short, externally located viewing tube before being returned to the medium in the main chamber. Changes of color in the window or in the tube would be indicative of the state of reduction and oxidation occurring in the reaction medium.

The reaction chamber would also be provided with a port 20 for receiving a reductant, such as a ferrous sulfate or other multi-valent oxidizable metal compound or free metal capable of reducing the metal contaminant. A second port 22, designated for pH control, is equipped with an automated programmable pump which would keep the initial pH of the reaction medium at an acidic level. After the reduction reaction has taken place, as monitored by color changes, the pH of the reaction medium would be raised to an alkaline level, above 7.0, through the addition of a base through the port 22. A clarifying agent, a flocculent and/or a precipitant would be added through a port 24 to aid in removal of the aggregated $Cr^{+3}$ compounds or other reduced contaminants which are formed in the reaction chamber. A source of hydrogen ions (protons) could be provided through a port 26 either electrochemically from a fuel cell or by addition of certain selected acids, such as dilute inorganic acids.

Another port 28 for introducing an electrical conductor into the reaction medium (not shown) can be provided to introduce the electrons needed for re-reduction of the oxidized reducing agent. The inflow of electrons and hydrogen ions (protons), along separate conduction paths, would also aid in maintaining the internal pH between a desired pH range of about 1.5 to about 6.5 and, preferably, between about 2.5 and 4.5. Generally, wherever possible, automatic and programmable devices would be used to control and regulate operations of the reactor. For example, proportional and programmable pH pump controllers would be used to adjust solution pH levels, and the same or other controllers can be used to operate at two or more pH ranges and to introduce or extract pre-set volumes of samples of solutions at pre-set times.

The volume of the reaction chamber would be determined primarily by volume rates of inflow and outflow, and these rates would be adjusted to satisfy demand need. These rates of flows can also be monitored, adjusted and regulated by other controllers. The reactor would also be provided with an outlet port 30 for the effluent water from which contaminants had been removed. The use of automated programmable controllers would allow the reactor to be used either in a batch-type mode or in a continuous flow mode. All settings and adjustments for the controller could most easily be determined and modified by a computer designed to handle inflow and outflow rates and levels, and ratios by means of both analog display and appropriate digital software programs.

FIG. 2 illustrates a slightly modified form of reactor in accordance with the present invention. In connection with the embodiment of FIG. 2, like reference numerals will be used on equivalent components compared to FIG. 1.

In the embodiment of FIG. 2, the reactor 10 is provided with a short sample withdrawal tube 50 located below the water level of water contained in the reactor chamber. A valve 52 will control inflow of water into a sampling tube 54, in which the water will remain for viewing purposes. A source of light 56 enables viewing of the water contents in the tube against a white background plate 58.

In accordance with the above-identified construction, the state of the reaction can be determined merely by examining the water within the sampling tube 54. The water in the sampling tube 54 is viewed against a bright background, such as a titanium white background, to estimate the level or concentration of the contaminants or the degree of reaction and, hence, degree of removal of the contaminants during the process. This procedure is quite advantageous because it allows an operator to estimate how far along the reaction has moved toward completion. In addition, it will advise an operator of approximately when and how much of the specific reagents must be injected through an appropriate port into the reaction chamber in order to keep the reaction going. For this purpose, the reactor 10 may be provided with an additional reagent port 60.

In place of the bypass tube 50 and the sampling tube 54, as shown in FIG. 2, it is also possible to merely obtain aliquots of samples from the reactor which could be removed through a non-corrosible tap. They would then be transferred to another container where the water would be viewed against a bright titanium white background in the same manner. It should also be understood that when the sample has been examined, it can then be discharged by means of an additional valve 62 at the lower end of the sampling tube. Otherwise, the sample removed from the reactor could be returned to the reactor.

3. Process Components and Parameters

The critical parameters for a suitable reductant are that it must be water-soluble and the active metal atom must be capable of existing in at least two different valence states. The lower valence state would correspond to the reduced state of the metal atom and the higher valence state would result from the metal atom yielding electrons to reduce the contaminant metal, thereby becoming oxidized.

As indicated previously, the solubility of the high valence state will determine whether or not the reductant is precipitated, or otherwise, remains in solution after removal of any precipitated materials and reduction by electrons introduced into the reactor chamber. Some of those salts which are capable of being used were itemized above.

There are actually a large number of available reductants which can be used in the present invention. Selected data are presented below for each of the metals listed in alphabetical order. These data include: the name of the metal, along with its chemical symbol, valence states, its atomic weight in daltons, and the group in the Periodic Table to which it belongs. In addition, the name and line formula of each metallic salt is given, followed by its molecular weight in daltons, along with the color of the reduced state of the metal in the salt. These data have been taken from the Handbook of Chemistry and Physics, published by the CRC Press. Any datum not listed means either that it is not available or it is uncertain. To the right of each of these potential metallic reductants, the available valence states are given and, particularly, the unoxidized state, the chemical formula and the color in the reduced state, if applicable.

1. Cerium, Ce (valence states: ITT, IV), 140.12, Rare Earth Group.
    (a) Ce(III) acetate, $Ce(C_2H_3O_2)_3$, 317.26, colorless.
    (b) Ce(III) acetate hydrate, $Ce(C_2H_3O_2)_3 \cdot 1\frac{1}{2}H_2O$, 344.28, white-reddish.
    (c) Ce(III) sulfate, $Ce_2(SO_4)_3$, 568.42, colorless to green.
    (d) Ce(III) sulfate pentahydrate, $Ce_2(SO_4)_3 \cdot 5H_2O$ 658.50.
    (e) Ce(III) sulfate octahydrate, $Ce_2(SO_4)_3 \cdot 8H_2O$, 712.54, pink.
    (f) Ce(III) sulfate nonahydrate, $Ce_2(SO_4)_3 \cdot 9H_2O$, 730.56.
2. Cobalt, Co (II, III), 58.933, Iron-Cobalt Group.
    (a) Co(II) acetate tetrahydrate, $Co(C_2H_3O_2)_2 \cdot 4H_2O$, 249.08, red-violet.
    (b) Co(II) bromide, $CoBr_2$, 218.75 green.
    (c) Co(II) bromide hexahydrate, $CoBr_2 \cdot 6H_2O$, 326.84, red-violet.
    (d) Co(II) chloride, $CoCl_2$, 129.84, blue.
    (e) Co(II) chloride dihydrate, $CoCl_2 \cdot 2H_2O$, 165.87, red-violet.
    (f) Co(II) chloride hexahydrate, $CoCl_2 \cdot 6H_2O$, 237.93, red.
    (g) Co(II) iodide ($\alpha$), $CoI_2$, 312.74, black.
    (h) Co(II) iodide ($\beta$), $CoI_2$, 312.74, yellow.
    (I) Co(II) iodide dihydrate, $CoI_2 \cdot 2H_2O$, 348.77, green.
    (j) Co(II) iodide hexahydrate, $CoI_2 \cdot 6H_2O$, 420.83, brown-red.
    (k) Co(II) nitrate hexahydrate, $Co(NO_3)_2 \cdot 6H_2O$, 291.04, red.
    (l) Co(II) sulfate, $Co(SO_4)$, 155.00, dark bluish.
    (m) Co(II) sulfate monohydrate, $Co(SO_4) \cdot H_2O$, 173.01, red.
    (n) Co(II) sulfate hexahydrate, $Co(SO_4) \cdot 6H_2O$, 263.09, red.
    (o) Co(II) sulfate heptahydrate, $Co(SO_4) \cdot 7H_2O$, 281.10, red-pink.
3. Europium, Eu (II, III), 151.96, Rare Earth Group.
    (a) Eu(II) bromide, $EuBr_2$, 311.78.
    (b) Eu(II) chloride, $EuCl_2$, 222.87, white.
    (c) Eu(II) iodide, $EuI_2$, 405.77, brown-olive green.
4. Iron, Fe (II, III), 55.847, Iron-Cobalt Group.
    (a) Fe(II) acetate tetrahydrate, $Fe(C_2H_3O_2)_2 \cdot 4H_2O$, 246.00 light green.
    (b) Fe(II) bromide, $FeBr_2$, 215.67, green-yellow.
    (c) Fe(II) chloride, $FeCl_2$, 126.75, green to yellow.
    (d) Fe(II) chloride dihydrate, $FeCl_2 \cdot 4H_2O$, 162.78. green.
    (e) Fe(II) chloride tetrahydrate, $FeCl_2 \cdot 4H_2O$, 198.81, blue-green.
    (f) Fe(II) iodide, $FeI_2$, 309.66, gray.
    (g) Fe(II) iodide tetrahydrate, $FeI_2 \cdot 4H_2O$ 381.72.
    (h) Fe(II) nitrate hexahydrate, $Fe(NO_3)_2 \cdot 6H_2O$, 287.95, green.
    (I) Fe(II) sulfate tetrahydrate, $Fe(SO_4) \cdot 5H_2O$, 224.01, green.
    (j) Fe(II) sulfate pentahydrate, $Fe(SO_4) \cdot 7H_2O$, 242.02, white.
    (k) Fe(II) sulfate heptahydrate, $Fe(SO_4) \cdot H_2O$, 278.05, blue-green.
5. Manganese, Mn (II, III), 54.938, Transition (VII b) Group.
    (a) Mn(II) acetate tetrahydrate, $Mn(C_2H_3O_2)_2 \cdot 4H_2O$, 245.08, pale red.
    (b) Mn(II) bromide, $MnBr_2$, 214.76, rose.
    (c) Mn(II) bromide tetrahydrate, $MnBr_2 \cdot 4H_2O$, 286.82, rose.
    (d) Mn(II) chloride, $MnCl_2$, 125.84, pink.
    (e) Mn(II) chloride tetrahydrate, $MnCl_2 \cdot 4H_2O$, 197.91, rose.
    (f) Mn(II) iodide, $MnI_2$, 308.75, rose.
    (g) Mn(II) iodide tetrahydrate, $MnI_2 \cdot 4H_2O$, 380.81, rose.
    (h) Mn(II) sulfate, $Mn(SO_4)$, 151.00, reddish.
    (I) Mn(II) sulfate monohydrate, $Mn(SO_4) \cdot H_2O$, 169.01, pale pink.
    (j) Mn(II) sulfate tetrahydrate, $Mn(SO_4) \cdot 4H_2O$, 223.06, pink.
    (k) Mn(II) sulfate pentahydrate, $Mn(SO_4) \cdot 5H_2O$, 241.08, rose.
    (l) Mn(II) sulfate heptahydrate, $Mn(SO_4)7H_2O$, 277.11, red.
6. Nickel, Ni (II, III), 58.71, Transition (VIII) Group.
    (a) Ni(II) acetate, $Ni(C_2H_3O_2)_2$, .176.80, green.
    (b) Ni(II) acetate tetrahydrate, $Ni(C_2H_3O_2)_2 \cdot 4H_2O$, 248.86, green.

(c) Ni(II) bromide, $NiBr_2$, 218.53, yellow brown.

(d) Ni(II) bromide trihydrate, $NiBr_2.3H_2O$, 272.57, yellowish green.

(e) Ni(II) chloride, $NiCl_2$, 129.62, yellow.

(f) Ni(II) chloride hexahydrate, $NiCl_2.6H_2O$, 237.70, green.

(g) Ni(II) iodide, $NiI_2$, 312.52, black.

(h) Ni(II) nitrate hexahydrate, $Ni(NO_3)_2.6H_2O$, 290.81, green.

(I) Ni(II) sulfate, $Ni(SO_4)$, 154.78, yellow.

(j) Ni(II) sulfate hexahydrate, $Ni(SO_4).6H_2O$, 262.86, green to blue.

(k) Ni(II) sulfate heptahydrate, $Ni(SO_4).7H_2O$, 280.88, green.

7. Platinum, Pt (II, III, IV), 195.09, Platinum Group.

(a) Pt(II) chloride, $PtCl_2$, 266.00, olive green.

(b) Pt(III) chloride, $PtCl_3$, 301.45, greenish black.

8. Praseodymium, Pr (III, IV), 140.907 Rare Earth Group.

(a) Pr(III) acetate trihydrate, $Pr(C_2H_3O_2)_3.3H_2O$, 372.09, green.

(b) Pr(III) chloride, $PrCl_3$, 247.27, blue green.

(c) Pr(III) chloride heptahydrate, $PrCl_3.7H_2O$, 373.37, green.

(d) Pr(III) iodide, $PrI_3$, 521.62, green.

(e) Pr(III) sulfate, $Pr_2(SO_4)_3$, 570.00, light green.

(f) Pr(III) sulfate pentahydrate, $Pr_2(SO_4)_3.5H_2O$ 660.08.

(g) Pr(III) sulfate octahydrate, $Pr_2(SO_4)_3.8H_2O$, 714.12, green.

9. Rhenium, Re (III, IV, V), 186.2, Transition (VII b) Group.

(a) Re(III) chloride, $ReCl_3$, 292.56, dark red.

(b) Re(IV) chloride, $ReCl_4$, 328.01, black.

10. Rhodium, Rh (II, III, IV), 102.905, Platinum Group.

(a) Rh(III) chloride hydrate, $RhCl_3.H_2O$, dark red.

(b) Rh(II) nitrate dihydrate, $Rh(NO_3)_2.2H_2O$, 262.905, red.

(c) Rh(III) sulfate tetrahydrate, $Rh_2(SO_4)_3.4H_2O$, 566.05, red.

(d) Rh(III) sulfate dodecahydrate, $Rh_2(SO_4)_3.12H_2O$, 710.18, pale yellow.

(e) Rh(III) sulfate pentadecahydrate, $Rh_2(SO_4)_3.15H_2O$, 764.22, light yellow.

11. Samarium, Sm (II, III), 150.35, Rare Earth Group.

(a) Sm(II) chloride, $SmCl_2$, 221.26, red-brown.

12. Terbium Tb (III, IV), 158.924, Rare Earth Group.

(a) Tb(III) bromide, $TbBr_3$ 398.65.

(b) Tb(III) chloride hexahydrate, $TbCl_3.6H_2O$, 373.78, colorless.

(c) Tb(III) fluoride, $TbF_3$, 215.92.

(d) Tb(III) iodide, $TbI_3$, 539.64.

(e) Tb(III) nitrate hexahydrate, $Tb(NO_3)_3.6H_2O$, 453.03, colorless.

(f) Tb(III) sulfate octahydrate, $Tb_2(SO_4)_3.8H_2O$, 750.16, white.

13. Tin, Sn (II, IV), 118.69, IV a Group Metals.

(a) Sn(II) bromide, $SnBr_2$, 278.51, pale yellow.

(b) Sn(II) chloride, $SnCl_2$, 189.60, white.

(c) Sn(II) fluoride, $SnF_2$, 156.69, white.

(d) Sn(II) sulfate, $Sn(SO_4)$, 214.75, white-yellowish.

14. Titanium, Ti (III, IV), 47.90, Transition (IV b) Group.

(a) Ti(III) chloride, $TiCl_3$, 154.26, dark yellow.

(b) Ti(III) fluoride, $TiF_3$, 104.90, red.

15. Ytterbium, Yb (II, III), 173.04, Rare Earth Group.

(a) Yb(II) bromide, $YbBr_2$, 332.86.

(b) Yb(II) chloride, $YbCl_2$, 243.95, green-yellow.

(c) Yb(II) iodide, $YbI_2$, 426.85, light yellow.

The various reducing agents identified above can be used individually or in combinations. Several of these reducing agents could be combined as a reductant for any metal contaminant of the type described herein. As a simple example, ferrous sulfate heptahydrate could be used in combination with ferrous acetate heptahydrate and ferrous chloride heptahydrate. This is also true when the reductant is comprised of different metals that are members of the same group of the Periodic Table.

The metallic salt reducing agents are effective and advantageous because they are frequently colored, as shown in the above list of reductants, even in a diluted form. Thus, in a reactor equipped with a lighted window and a short external viewing tube, the reactants would also provide distinct changes of color characteristic of the redox reactions as they occur. The changes of color, and/or the appearance or disappearance of color, would indicate that the metal had been converted to its oxidized state and that the metal contaminant had been reduced. Generally, although not in all cases, the reductant forms of hydroxides are co-precipitated with the hydroxides of the reduced contaminant metal. The remaining (non-precipitated) oxidized metal reductant would be replenished and/or re-converted by reduction from its higher valence state to its lower or reduced valence state. For iron salts, color changes from yellow-green to amber, depending on concentrations of specific iron salt ions are also associated with conversion of $Fe^{+2}$ to $Fe^{+3}$.

The complexing agent would normally be a dicarboxylic acid or a tricarboxylic acid. These particular acids act as chelating or sequestering agents and thereby stabilize the reductant, but do not interfere with their reducing properties. Some of the suitable sequestering agents which may be used include, for example, fumaric(trans-1,2-ethylenedicarboxylic) acid, malic(hydroxysuccinic) acid, and succinic(ethanedicarboxylic) acid. Some of the tricarboxylic acids which may be used include aconitic acid (1-propene-1,2,3-tricarboxylic acid) and citric acid (2-hydroxy-1,2,3-propanetricarboxylic acid).

Maintaining an acid pH roughly between 1.0 to 6.5 and, preferably, between 2.5 to 4.5, in the reactor is desirable because the carboxyl groups of these dicarboxylic and tricarboxylic acids would be protonated relative to their pK values. In this way, the metal ion of the reducing agent could enter into an exchange reaction with the protons of the carboxylic acid groups which would provide stabilization of the reducing agents.

To maintain an acidic milieu in the reaction medium, diluted inorganic acids, such as hydrochloric acid or sulfuric acid, would be added to the reaction chamber to produce the desired pH range and maintain the stability of the metal contaminants, both in their oxidized and reduced forms. Sodium or potassium hydroxide could also be added to neutralize and alkalinize the reactor constituents to allow for precipitation of the reduced contaminant, such as $Cr^{+3}$, in the form of chromium hydroxide.

It may be desirable to determine the completeness and effectiveness of the reaction which is occurring. For this purpose, aliquots of the water in the influent and effluent water lines would be monitored on a periodic basis by withdrawal of samples and using atomic absorption spectrometry for analyses. A graphite furnace should be used with any suitable spectrometer to insure that temperatures would be sufficiently high and stable to obtain clear and unambiguous spectra.

Conversion of the oxidized metal contaminant to the reduced contaminant state would be followed by neutralization with a base, such as sodium hydroxide or potassium hydroxide in order to raise the pH to a level above 7, e.g., 8–10. As a result, chromium hydroxide and other metal hydroxides would precipitate from the solution in the reactor and the precipitate would be removed by a combination of conventional methods, including the addition of flocculents and/or precipitants, followed by settling out and filtration.

One of the unique aspects of the present invention is that the reductant can be recycled by reconverting the $Fe^{+3}$ after reduction of the metal contaminant back to $Fe^{+2}$, or of the $Co^{+3}$ to $Co^{+2}$, or similarly with other reductants. A shift of pH from a basic range back to an acidic range of pHs would also be effected through separate electron and proton conductors or conduction paths introduced to the reactor from a hydrogen fuel cell or other comparable device. Introduction of electrons into the reactor not only reduces the spent or oxidized reducing agents, but the addition of the protons returns the reactor contents to a desired acid range of pH and re-protonates the dicarboxylic acids and the tricarboxylic acids. This will, in turn, regenerate the capacity to form complexes through an exchange of carboxyl hydrogens with the metal ions of the reducing agents.

One form of hydrogen fuel cell most easily adaptable to provide both electrons and protons through two separate conduction paths into the reactor is described herein. Normally, hydrogen gas enters a fuel cell and makes contact with an anode, which serves as an electrocatalyst. This catalyst consists of a porous platinum (Pt) or platinum-iridium (Pt—Ir) surface, made porous by a thin layer of platinum (or platinum-iridium) black. Platinum (or platinum-iridium) black consists of finely reduced metal particles with an average aerodynamic diameter well below 100 microns. The porosity of this layer facilitates the diffusion of influent hydrogen gas to the catalytic surface, ensuring a more complete and rapid reaction releasing protons and electrons. The porosity also makes it possible for the fuel cell to operate at lower temperatures, well below 100° C., thereby prolonging the operational life of the cell. The electrocatalyst of the cathode is also made of Pt or of Pt—Ir coated with Pt or Pt—Ir.

The anode and cathode serve dual functions: as electrocatalysts and as physical barriers between which the electrolyte is contained. Some of the electrons released at the catalytic surface of the anode are conducted away from the fuel cell into the reactor through an external circuit. The protons are conducted from the anode through the electrolyte, consisting of an ion exchange membrane constructed of polymeric material containing fluorinated sulfonic acid residues, which appear to be superb proton conductors. Some of these protons can be led away from the fuel cell to the reactor through an external conduction path consisting of the fluorinated sulfonic polymeric material.

In the fuel cell's usual mode of functioning, oxygen gas (the oxidant) is introduced at the cathode, where oxygen atoms released from the catalytic surface react with electrons brought back into the cell by means of an external circuit, and with protons diffusing through the electrolyte, to produce electrically neutral water molecules. In theory, the fuel cell would continue to operate as long as the fuel (hydrogen gas) and the oxidant (oxygen gas) are available to the electrodes. In reality, however, the life of the cell will depend on corrosion and the degradation of the system it induces, as well as the breakdown and malfunctioning of the cell's components.

As noted above, the electrons (e's) are required to re-reduce the spent (oxidized) reducing agent. The protons ($H^+$'s are needed to re-protonate the di- and/or tricarboxylic acids, thereby regenerating their capacity to form complexes through an exchange of carboxyl hydrogens with the metals, e.g., Fe II or Co II, of the reducing agent. These acids were left in their carboxylate forms following the use of base to alkalinize the reaction mixture, which allowed Cr III and (ferric or cobaltic) hydroxides to coprecipitate for removal from the reactor.

EXAMPLES

The invention is further illustrated by, but not limited to, the following examples:

Example I

Determination of Hexavalent Chromium in Water with a Ferrous Reductant.

A test of this visual determination was conducted in connection with the reduction of $Cr^{+6}$ to $Cr^{+3}$ using an $Fe^{+2}$ reducing agent with the latter being oxidized in the reaction to $Fe^{+3}$. As indicated above, the ferrous ion was ferrous sulfate heptahydrate with a formula weight of 278.01 daltons. The oxidized chromium used for this test was sodium chromate tetrahydrate with a formula weight of 234.06 daltons and the reduced chromium was chromium trichloride with a formula weight of 158.38 daltons.

Approximately 28.35 grams, one ounce, of ferrous sulfate tetrahydrate was diluted in a weight-to-volume measure of 100 milliliters with filtered water. Gentle warming was required to completely dissolve the ferrous sulfate heptahydrate. The original undiluted solution had a very weak greenish yellow color.

A preliminary test with a distinctly green solution of the reduced chromium salt, chromium trichloride, showed no reaction with the ferrous ions and, therefore, no specific dilutions of this salt were made for further testing.

The formula weight of the ferrous sulfate heptahydrate in the amount of 278.01 grams yields 56.01 grams of ferrous iron. As a result, one ounce or 28.35 grams of ferrous sulfate heptahydrate yields 5.71 grams of ferrous iron when dissolved in the filtered water. Through a sequence of 50-fold dilutions, 0.0036 micrograms per liter was derived, equivalent to 0.0036 parts per billion.

The water which was used for the dilutions was filtered through an Equinox-10 three stage filtration unit. The first stage contained a granular high-density medium of fused purified zinc and copper for reducing chlorine and inhibiting bacterial growth. The second stage contained a ceramic-impregnated titanium silicate having materials which irreversibly bind to dissolved metals. The third stage included a blend of two kinds of high-grade granular activated carbon to enhance adsorption of organic contaminants and pollutants, such as trichloroethylene and benzene. The water was shown to be completely free of $Cr^{+6}$ when tested qualitatively with a high concentration of $Fe^{+2}$.

During the test, a visually discernible amber color formed in solutions of $Cr^{+6}$ when viewed against a white background. The $Cr^{+6}$ concentrations ranged from 0.0014 parts per billion to about 442,000 parts per billion. The $Fe^{+2}$ concentrations changed the color of the $Cr^{+6}$ solutions to shades of amber. The results suggested that the concentrations of $Fe^{+2}$ yield a wide range of amber colors with various concentrations between $4 \times 10^{-4}$ M and $8 \times 10^{-6}$ M ferrous iron. Thus, the test appeared to be quite valid for the detection of reducible metal contaminants, such as $Cr^{+6}$ in drinking water.

Example II

Determination of Hexavalent Chromium in Water with a Cobaltous Reductant.

A test using visual determination was conducted in connection with the reduction of $Cr^{+6}$ to $Cr^{+3}$ using a $Co^{+2}$ reducing agent and with the latter being oxidized in the reaction to $Co^{+3}$. As indicated above, the cobaltous acetate tetrahydrate had a weight of 249.08 daltons. The oxidized chromium which was used for this test was sodium chromate tetrahydrate with a formula weight of 234.06 daltons and the reduced chromium was chromium trichloride with a formula weight of 158.38 daltons.

Approximately 28 grams of cobalt acetate tetrahydrate was diluted in a weight-to-volume measure of 100 milliliters with filtered water. Gentle warming was required to completely dissolve the cobalt salt. The original undiluted solution had a red-violet color in water.

A preliminary test with a distinctly green solution of the chromium (Cr III) salt showed no reaction with the cobalt ions and, therefore, following one 50-fold dilution, no further dilutions of this salt were made for further testing.

The formula weight of cobaltous acetate tetrahydrate, namely, 249.08 grams, yields 58.933 grams of cobalt which gives essentially the same final dilution as obtained with ferrous sulfate heptahydrate. The formula weight of 234.06 daltons of sodium chromate tetrahydrate yields 52.06 grams of $Cr^{+6}$. As a result, 10 grams of this chromate dissolved in 100 milliliters of filtered water (weight-to-volume), followed by a series of five 50-fold dilutions, yielded a final concentration of $Cr^{+6}$ of $7.13 \times 10^{-2}$ micrograms per liter or 0.071 parts per billion.

The water which was used for the dilutions was filtered through an Equinox-10 three stage filtration unit. The first stage contained a granular high-density medium of fused purified zinc and copper for reducing chlorine and inhibiting bacterial growth. The second stage contained a ceramic-impregnated titanium silicate having materials which irreversibly bind to dissolved metals. The third stage included a blend of two kinds of high-grade granular activated carbon to enhance adsorption of organic contaminants and pollutants, such as trichloroethylene and benzene. The water was shown to be completely free of $Cr^{+6}$ when tested qualitatively with a high concentration of $Fe^{+2}$.

During the test, a visually discernible blue-green color formed in the solutions of $Cr^{+6}$ when viewed against a white background. The $Cr^{+6}$ concentrations ranged from 0.0014 parts per billion to about 442,000 parts per billion. The $Co^{+2}$ concentrations changed the color of the $Cr^{+6}$ solutions to shades tinged with a blue-green cast. The results suggested that the various concentrations of $Co^{+2}$ yield a wide range of colors with different concentrations of $Cr^{+6}$. Thus, the test appeared to be quite valid for the detection of reducible metal contaminants, such as $Cr^{+6}$, in drinking water.

Example III

On-Line Conversion of Hexavalent Chromium to Trivalent Chromium in Water.

This example describes an on-line conversion of hexavalent chromium to trivalent chromium in water.

The water to be treated normally comes from a variety of sources used for municipal or community drinking water. These sources may include water from rivers, lakes, aqueducts, reservoirs, aquifers, wells and other ground waters. The combined volumes of water from these sources enters the treatment-distribution facility serving the drinking water needs of the residents and others in the municipality or community. There the water enters the reaction chamber, either by batch-type or continuous flow mode, depending, in part, on the combined volume and water to be treated and the expected level or concentration of the suspected contaminant. Treatment comprises adjustment to a pH range of 1.5 to 6.5, preferably between 2.5 and 4.5. This insures solubility of the metal contaminants and of the reagents added to the reaction chamber. The reducing agent or combination of agents is added, along with the sequestering agent(s) to stabilize the components of the redox system. A preferred reducing agent for this purpose is ferrous sulfate heptahydrate.

The contents of the reaction chamber are kept in constant motion by a magnetic stirrer sealed into the bottom of the chamber. This device eliminates the need for a dispersing agent, as required when testing small volumes of water containing suspected contaminants. Thereafter, periodic testing and/or visualization of the contents of the reaction chamber insures completion of the redox reaction. Following adjustment of the reactor's contents to pH's above 7, precipitated mixed hydroxides of the metal contaminant and the reducing agent(s) are removed by conventional means. Electrons and protons generated by a fuel cell are introduced into the reaction chamber. The electrons re-reduce the oxidized reductant(s). The protons, introduced into the chamber by another conduction path from the fuel cell, re-protonate the di- and tri-carboxylic acid sequestering agents to facilitate exchanges with the metallic atoms of the reductant(s). This overall cycle is repeated until testing and/or visualization confirms completion of the redox reaction.

Thus, there has been illustrated and described a unique and novel method for determination of the presence of metal contaminants in water and a unique and novel method and system for removal of metal contaminants from water, which thereby fulfills all of the objects and advantages which have been sought. It should be understood that many changes, modifications, variations and other uses and applications will become apparent to those skilled in the art after considering this specification and the accompanying figures. Therefore, any and all such changes, modifications, variations and other uses and applications which do not depart from the spirit and scope of the invention are deemed to be covered by the invention.

Having thus described the invention, what I desire to claim and secure by Letters Patent is:

1. A method of making a determination for a presence of a harmful water-soluble multi-valent, and ionically reducible metal contaminant in water, said method comprising:

a) introducing into a sample of the water to be tested a composition comprising a water-soluble, multi-valent, metal or metal anion reducing agent which will reduce the metal contaminant to a lower valence state with the reducing agent becoming oxidized to a higher valence state, and where the metal or metal anion reducing agent is responsible for substantially all of the metal contaminate reduction;

b) maintaining said water containing composition at a pH substantially below 7.0;

c) allowing for a physically observable change in said water to provide readily visual indication of the presence of the potentially harmful metal contaminant based on said change.

2. The method for determining a presence of a metal contaminant in water of claim 1 further characterized in that said metal contaminant is a contaminant which comprises a metal selected from the group consisting of arsenic, chromium and mercury and salts thereof.

3. The method for determining a presence of a metal contaminant in water of claim 1 further characterized in that said reducing agent is a free metal or metal salt selected from the class consisting of iron and iron salts and cobalt and cobalt salts.

4. The method for determining a presence of a metal contaminant in water of claim 1 further characterized in that said reducing agent is a metal or metal salt selected from the class consisting of cerium, cobalt, europium, iron, manganese, nickel, platinum, praseodymium, rhenium, rhodium, samarium, terbium, tin, titanium, and ytterbium.

5. The method for determining a presence of a metal contaminant in water of claim 1 further characterized in that said composition comprises a member selected from the class consisting of sequestering agents, flocculating agents and precipitating agents.

6. The method for determining a presence of a metal contaminant in water of claim 5 further characterized in that said composition also comprises a dispersing agent.

7. The method for determining a presence of a metal contaminant in water of claim 6 further characterized in that said composition is present in the form of a water-soluble tablet capable of being introduced into a sample of water to be tested.

8. The method for determining a presence of a metal contaminant in water of claim 1 further characterized in that said change is a visual change in the water.

9. The method for determining a presence of a metal contaminant in water of claim 1 further characterized in that said change is a presence of suspended solid matter in the water.

10. A method for testing for the presence of a potentially harmful water soluble multi-valent and ionically reducible metal containing contaminant capable of being reduced, said method comprising:

a) introducing into a sample of the water to be tested a composition to render a water containing medium and which composition is a water soluble, multi-valent metal or metal anion reducing agent and will reduce the metal contaminant to a lower or reduced valence and with the reducing agent being oxidized in a higher valence state and concomitantly provide a visually apparent change in the water containing medium based on a potential presence of the metal contaminant in the water; and b) establishing an acid pH in the water containing medium and avoiding the formation of any suspension in the water containing medium which would obscure the visually apparent change which may take place.

11. The method of testing for the presence of a potentially harmful metal constituent in water of claim 10 further characterized in that said method comprises also introducing into the sample of water to be tested a member selected from the class consisting of sequestering agents and flocculating agents.

12. The method of testing for the presence of a potentially harmful metal constituent in water of claim 10 further characterized in that said method comprises introducing into the sample of water to be tested a sequestering agent to enable efficient interaction of the constituents in the water and complete reduction of the metal contaminant.

13. The method of testing for the presence of a potentially harmful metal constituent in water of claim 10 further characterized in that said method comprises detecting for the presence of any one of arsenic, chromium and mercury or salts thereof.

14. The method of testing for the presence of a potentially harmful metal constituent in water of claim 10 further characterized in that said method comprises adding to said sample of water a metal anion reducing agent selected from the class consisting of iron and cobalt.

15. The method of testing for the presence of a potentially harmful metal constituent in water of claim 10 further characterized in that said method comprises introducing into the sample of water a metal anion reducing agent selected from the class consisting of cerium, cobalt, europium, iron, manganese, nickel, platinum, praseodymium, rhenium, rhodium, samarium, terbium, tin, titanium, and ytterbium.

16. A method for eliminating from a body of water a potentially harmful multi-valent water-soluble metal contaminant capable of being reduced to a lower valence state, said method comprising:

a) introducing into said body of water a composition comprising a water-soluble, multi-valent, metal-containing reducing agent capable of reducing the metal contaminant to a lower valence state;

b) maintaining the pH of the body of water with a reducing agent therein in a first pH range to facilitate reduction of the metal contaminant;

c) also introducing into said body of water a flocculating and precipitating ingredient which enables consolidation of the reduced metal contaminant in the body of water;

d) maintaining the pH of the body of water after introduction of the flocculating and precipitating agent at a second pH range to facilitate precipitation of the reduced metal contaminant; and e) removing the reduced metal contaminant from the body of water.

17. The method for eliminating from a body of water the potentially harmful multi-valent water-soluble contaminant of claim 16 further characterized in that said method causes precipitation of reduced contaminants in the water at an acid pH, and the method comprises reducing the pH of the second pH range which is alkaline to aid in removal of the reduced constituents from the body of water.

18. The method for eliminating from a body of water the potentially harmful multi-valent water-soluble contaminant of claim 16 further characterized in that said metal contaminant is a contaminant which comprises a metal selected from the group consisting of arsenic, chromium and mercury or salts thereof.

19. The method for eliminating from a body of water the potentially harmful multi-valent water-soluble contaminant of claim 16 further characterized in that said reducing agent is a metal or metal salt selected from the class consisting of cerium, cobalt, europium, iron, manganese, nickel, platinum, praseodymium, rhenium, rhodium, samarium, terbium, tin, titanium, and ytterbium.

20. The method for eliminating from a body of water the potentially harmful multi-valent water-soluble contaminant of claim 17 further characterized in that said method comprises adding to the body of water a sequestering agent.

21. The method for eliminating from a body of water the potentially harmful multi-valent, water-soluble contaminant of claim 20 further characterized in that said method also comprises adding a dispersant to the body of water.

22. A method for detecting for the presence of a potentially harmful water soluble multi-valent metal contaminant in water by observing the presence of a prominent visual change in the water if the harmful metal contaminant is present in the water, said method comprising:
  a) introducing into a sample of the water a tableted composition having a water soluble multi-valent and ionically reducible metal or metal-anion reductant capable of reducing the metal contaminant to a reduced state;
  b) generating a visually apparent physical change in the water if the contaminant is present; and
  c) introducing a stabilizing agent into the water.

23. The method of claim 22 further characterized in that said method comprises introducing in said tableted composition a dispersing agent and thereby obtaining rapid mixing and dispersal of the reducing agent throughout the sample of water to be tested.

24. The method of claim 22 further characterized in that said method comprises introducing said reducing agent in the form of a metal or metal salt selected from the class consisting of ferrous and cobalt metals and metal salts.

25. The method of claim 23 further characterized in that said method comprises introducing said dispersing agent in the form of sodium bicarbonate.

26. The method of claim 22 further characterized in that said method comprises forming a suspension of solid matter in the water and the visual determination is achieved by observation of a suspension of solid matter in water.

27. The method of claim 22 further characterized in that said metal contaminant is a contaminant which comprises a metal selected from the group consisting of arsenic, chromium and mercury or salts thereof.

28. A method for eliminating from a body of water a potentially harmful multi-valent water-soluble metal contaminant capable of being reduced to a lower valence state, said method comprising:
  a) introducing into said body of water a composition comprising a water-soluble, multi-valent, metal-containing reducing agent capable of reducing the metal contaminant to a lower valence state and oxidizing the reducing agent;
  b) also introducing into said body of water a flocculating and precipitating ingredient which enables consolidation of the reduced metal contaminant in the body of water;
  c) removing the reduced metal contaminant from the body of water; and
  d) recycling the reducing agent by reducing the reducing agent from the oxidized state back to its reduced state to thereby regenerate the capacity of the reducing agent to further reduce a metal contaminant.

29. The method for eliminating from a body of water the potentially harmful multi-valent water-soluble contaminant of claim 28 further characterized in that said method causes precipitation of reduced contaminants in the water and permits removal of the reduced constituents from the body of water.

30. The method for eliminating from a body of water the potentially harmful multi-valent water-soluble contaminant of claim 28 further characterized in that said metal contaminant is a contaminant which comprises a metal selected from the group consisting of arsenic, chromium and mercury or salts thereof.

31. The method for eliminating from a body of water the potentially harmful multi-valent water-soluble contaminant of claim 28 further characterized in that said reducing agent is a metal or metal salt selected from the class consisting of cerium, cobalt, europium, iron, manganese, nickel, platinum, praseodymium, rhenium, rhodium, samarium, terbium, tin, titanium, and ytterbium.

32. The method for eliminating from a body of water the potentially harmful multi-valent water-soluble contaminant of claim 28 further characterized in that said composition comprises a member selected from the class consisting of sequestering agents and flocculating and precipitating agents.

33. The method for eliminating from a body of water the potentially harmful multi-valent, water-soluble contaminant of claim 28 further characterized in that said composition also comprises a dispersant.

34. A method for eliminating from water multi-valent, water-soluble metal contaminants which are reducible in the presence of a selected reducing agent, said method comprising:
  a) providing a treatment chamber for a body of water to be treated for elimination of said harmful metal constituent;
  b) introducing into said treatment chamber a water-soluble, multi-valent metal reducing agent able to react with the metal contaminant;
  c) effectively reducing the metal contaminant to a reduced valence state and simultaneously oxidize the reducing agent to a higher oxidized valence state;
  d) introducing into the body of water an ingredient which permits separation of solid constituents formed through by the reaction of the metal contaminant with the reducing agent; and
  e) discharging and removing any separated solid constituents from the body of water.

35. The method for eliminating multi-valent metal contaminants from water of claim 34 further characterized in that said metal contaminant is a contaminant which comprises a metal selected from the group consisting of arsenic, chromium and mercury or salts thereof.

36. The method for eliminating multi-valent metal contaminants from water of claim 34 further characterized in that said method comprises a window enabling viewing an indication of the presence of the metal contaminant by observing a visual change in a reaction medium therein.

37. The method for eliminating multi-valent metal contaminants from water of claim 34 further characterized in that said reducing agent is a finely divided free metal or metal salt selected from the class consisting of iron and iron salts and cobalt and cobalt salts.

38. The method for eliminating multi-valent metal contaminants from water of claim 34 further characterized in that said reducing agent is a metal or metal salt selected from the class consisting of cerium, cobalt, europium, iron, manganese, nickel, platinum, praseodymium, rhenium, rhodium, samarium, terbium, tin, titanium, and ytterbium.

39. The method for eliminating multi-valent metal contaminants from water of claim 34 further characterized in that said ingredient comprises a member selected from the class consisting of sequestering agents, precipitating agents and flocculating agents.

40. The method for eliminating multi-valent metal contaminants from water of claim 34 further characterized in that said metal contaminant is a metal selected from the class consisting of arsenic, chromium, mercury or salts thereof, and that said reducing agent is a finely divided free metal or metal salt selected from the class consisting of iron and iron salts and cobalt and cobalt salts.

41. A method of making a determination for a presence of a harmful water-soluble multi-valent, and ionically reducible metal contaminant in water, said method comprising:

a) introducing into a sample of the water to be tested a composition comprising a water-soluble, multi-valent, metal-containing reducing agent which will reduce the metal contaminant to a lower valence state;

b) also introducing into said sample of water a dispersing agent and a member selected from the class consisting of sequestering agents, flocculating agents and precipitating agents; and c) allowing for a change in said water to provide indication of the presence of the potentially harmful metal contaminant based on said change.

42. The method determining a presence of a metal contaminant in water of claim 41 further characterized in that said composition is present in the form of a water-soluble tablet capable of being introduced into a sample of water to be tested.

43. A method for eliminating from a body of water a potentially harmful multi-valent water-soluble metal contaminant capable of being reduced to a lower valence state, said method comprising:

a) introducing into said body of water a composition comprising a water-soluble, multi-valent, metal-containing reducing agent capable of reducing the metal contaminant to a lower valence state;

b) also introducing into the body of water a dispersing agent to obtain dispersal of the reducing agent in the body of water; and c) also introducing into said body of water a flocculating and precipitating ingredient which enables consolidation of the reduced metal contaminant in the body of water; and d) removing the reduced metal contaminant from the body of water.

* * * * *